(12) United States Patent
He

(10) Patent No.: US 11,904,274 B2
(45) Date of Patent: Feb. 20, 2024

(54) AIR PURIFIER AND WATER PURIFICATION SYSTEM

(71) Applicant: HUNAN CHANGXIANG INDUSTRIAL CO., LTD, Hunan (CN)

(72) Inventor: Yingbin He, Hunan (CN)

(73) Assignee: HUNAN CHANGXIANG INDUSTRIAL CO., LTD, Hunan (CN)

( * ) Notice: Subject to any disclaimer, the term of this patent is extended or adjusted under 35 U.S.C. 154(b) by 526 days.

(21) Appl. No.: 17/262,698

(22) PCT Filed: Jul. 27, 2018

(86) PCT No.: PCT/CN2018/097572
§ 371 (c)(1),
(2) Date: Jan. 22, 2021

(87) PCT Pub. No.: WO2020/019323
PCT Pub. Date: Jan. 30, 2020

(65) Prior Publication Data
US 2021/0162342 A1    Jun. 3, 2021

(51) Int. Cl.
*B01D 53/78* (2006.01)
*A61L 9/20* (2006.01)
(Continued)

(52) U.S. Cl.
CPC .............. *B01D 53/78* (2013.01); *A61L 9/015* (2013.01); *A61L 9/20* (2013.01); *B01D 53/007* (2013.01);
(Continued)

(58) Field of Classification Search
CPC ...... B01D 53/78; B01D 53/007; B01D 53/72; B01D 2251/104; B01D 2257/91;
(Continued)

(56) References Cited

U.S. PATENT DOCUMENTS 8,444,922 B2    5/2013   Kusuura

FOREIGN PATENT DOCUMENTS

CN          2756231 Y       2/2006
CN          201834824 U     5/2011
(Continued)

OTHER PUBLICATIONS

Machine-generated English translation of CN 106498679, generated on Jul. 24, 2023.*

(Continued)

*Primary Examiner* — Fred Prince
(74) *Attorney, Agent, or Firm* — DITTHAVONG, STEINER & MLOTKOWSKI

(57) ABSTRACT

An air purifier and a water purification system, the air purifier comprises a housing, a vacuum air pump and an ozone generator, at least one ultraviolet lamp tube is provided in the housing, an air inlet is provided at a position of the housing corresponding to one end of the ultraviolet lamp tube, at least one air outlet is provided at a position of the housing corresponding to the other end of the ultraviolet lamp tube, and an air filter unit is communicated with the air inlet by means of an air drying unit; and an air inlet end of the vacuum air pump is communicated with an inner cavity of the housing, an air outlet end of the vacuum air pump is communicated with an air inlet end of the ozone generator, and an air outlet end of the ozone generator is communicated with the inner cavity of the housing.

10 Claims, 2 Drawing Sheets

(51) Int. Cl.
*C02F 1/32* (2023.01)
*B01D 53/00* (2006.01)
*A61L 9/01* (2006.01)
*B01D 53/72* (2006.01)
*C02F 1/78* (2023.01)
*A61L 9/015* (2006.01)

(52) U.S. Cl.
CPC ............... *B01D 53/72* (2013.01); *C02F 1/32* (2013.01); *A61L 2209/212* (2013.01); *B01D 2251/104* (2013.01); *B01D 2257/91* (2013.01); *B01D 2258/06* (2013.01); *B01D 2259/804* (2013.01); *C02F 1/78* (2013.01); *C02F 2303/04* (2013.01)

(58) Field of Classification Search
CPC .......... B01D 2258/06; B01D 2259/804; A61L 9/015; A61L 9/20; A61L 2209/212; C02F 1/32; C02F 1/78; C02F 2303/04

USPC ... 210/192.1, 748.1, 748.11, 748.12, 748.13, 210/748.15, 748.19; 55/315

See application file for complete search history.

(56) References Cited

FOREIGN PATENT DOCUMENTS

| | | | |
|---|---|---|---|
| CN | 106498679 | * | 3/2017 |
| CN | 207108712 U | | 3/2018 |

OTHER PUBLICATIONS

Machine-generated English translation of CN 2756231, generated on Jul. 24, 2023.*

International Search Report issued in corresponding Application No. PCT/CN2018/097572 dated Apr. 23, 2019.

* cited by examiner

AIR PURIFIER AND WATER PURIFICATION SYSTEM

CROSS-REFERENCE TO RELATED APPLICATIONS

The present application is a U.S. National Phase of PCT/CN2018/097572 filed on Jul. 27, 2018. The disclosure of the PCT Application is hereby incorporated by reference into the present Application.

FIELD OF THE INVENTION

The present invention particularly relates to an air purifier and a water purification system.

BACKGROUND OF THE INVENTION

In an existing water purification tower, an ultraviolet lamp tube is provided at a top of an inner cavity of the water purification tower, and an ozone inlet and an air inlet are provided at the top of the water purification tower. Filtered and dried air enters the water purification tower via the air inlet, meanwhile, ozone enters the water purification tower via the ozone inlet, and after sterilized by ozone and the ultraviolet lamp tube, the air forms a protective barrier above a water surface of the water purification tower to protect purified water in the water purification tower from being polluted.

The existing water purification tower with such a structure cannot ensure that the purified water in the water purification tower is not polluted. The reason lies in that the air entering the water purification tower is not sterilized, i.e. the air entering the water purification tower itself carries harmful substances such as bacteria, and after the air enters the water purification tower, it is most likely to pollute water before the sterilization of the ozone and ultraviolet is exerted. Therefore, the existing water purification tower cannot achieve the effect of protecting the purified water therein from being polluted.

SUMMARY OF THE INVENTION

The purpose of the present invention is to, in response to the above shortcomings of the prior art, provide an air purifier and a water purification system, which can stop air from polluting purified water in a water purification tower from the source and ensure that the purified water in the water purification tower is not polluted.

In order to solve the above technical problems, the technical solution adopted by the present invention is:

An air purifier is structurally characterized by including a housing, a vacuum air pump and an ozone generator, at least one ultraviolet lamp tube is provided in the housing, an air inlet is provided at a position of the housing corresponding to one end of the ultraviolet lamp tube, at least one air outlet is provided at a position of the housing corresponding to the other end of the ultraviolet lamp tube, and an air filter unit is communicated with the air inlet by means of an air drying unit; and an air inlet end of the vacuum air pump is communicated with an inner cavity of the housing, an air outlet end of the vacuum air pump is communicated with an air inlet end of the ozone generator, and an air outlet end of the ozone generator is communicated with the inner cavity of the housing.

With the above structure, filtered and dried air enters the housing from one end of the ultraviolet lamp tube and flows through the ultraviolet lamp tube along the length direction (since the air flows along the length direction, the sterilization time is long and the sterilization effect is good), meanwhile, the air sterilized by the ultraviolet lamp tube in the housing enters the ozone generator, the produced ozone enters the housing, and the sterilized air finally flows out of the air outlet. The air flowing out of the air outlet of the air purifier is delivered to a water purifier, which can stop the air from polluting purified water in the water purification tower from the source and ensure that the purified water in the water purification tower is not polluted. In addition, the air purifier can also provide the sterilized air for any device in demand.

Further, at least one first division plate is provided in the inner cavity of the housing and is along the length direction of the ultraviolet lamp tube, and the first division plate is perpendicular to the length direction of the ultraviolet lamp tube.

With the above structure, the air at the tail end of the air flow path in the housing is preferentially delivered out for use, with good sterilization effect.

Further, the first division plate is provided with one or more first through holes.

At least one first division plate divides the housing into one or more cavities, and the adjacent cavities are communicated with each other through the first through hole to provide a path for air flow.

As a preferred mode, the housing is cylindrical or cubic.

As a preferred mode, the length direction of the housing is parallel to or perpendicular to the horizontal plane.

Based on the same inventive concept, the present invention further provides a water purification system, which includes a water purification tower and further includes the air purifier, and one air outlet of the air purifier is communicated with an inner cavity of the water purification tower.

Further, an air duct is provided in the inner cavity of the water purification tower, the air outlet is communicated with one end of the air duct, and the other end of the air duct is provided with a sand air-diffuser.

The sterilized air provided by the air purifier is injected into purified water through the sand air-diffuser to sterilize the purified water.

Further, a diversion pipe is provided in the inner cavity of the water purification tower, a top of the water purification tower is provided with a purified water inlet, the purified water inlet is communicated with one end of the diversion pipe, the other end of the diversion pipe extends to a bottom of the water purification tower, and a side wall of the diversion pipe is provided with a through slot along the length direction.

Since ozone is decomposed over time, the water at the bottom of the water purification tower is prone to deactivation due to long-time deposition. In the prior art, ozone water enters from the purified water inlet and freely falls into the inner cavity of the water purification tower from above, the newly injected ozone water is not mixed with the water deposited at the bottom of the water purification tower, and the water at the bottom of the water purification tower easily forms dead water to affect water quality. In the present invention, the diversion pipe introduces ozone water to the bottom of the water purification tower, and the ozone water is injected throughout the water purification tower along the length direction by means of the through slot, thereby preventing the formation of dead water in the water purification tower and ensuring water quality.

Further, at least one second division plate is provided in the inner cavity of the water purification tower and is along the length direction of the water purification tower, and the second division plate is perpendicular to the length direction of the water purification tower.

With the above structure, the purified air at the tail end of the purified air flow path in the housing is preferentially delivered out for use, which further prevents the formation of dead water and further ensures water quality.

Further, the second division plate is provided with one or more second through holes. At least one second division plate divides the water purification tower into one or more cavities, and the adjacent cavities are communicated with each other through the second through hole to provide a path for purified water and air flow.

Compared with the prior art, the present invention can stop air from polluting purified water in the water purification tower from the source, ensure that the purified water in the water purification tower is not polluted, prevent the formation of dead water in the water purification tower, and ensure water quality.

In the figures: 1 represents housing, 2 represents vacuum air pump, 3 represents ozone generator, 4 represents ultraviolet lamp tube, 5 represents air inlet, 6 represents air outlet, 7 represents air filter unit, 8 represents air drying unit, 9 represents first division plate, 901 represents first through hole, 10 represents water purification tower, 11 represents air duct, 12 represents sand air-diffuser, 13 represents diversion pipe, 1301 represents through slot, 14 represents purified water inlet, 15 represents second division plate, 1501 represents second through hole.

DETAILED DESCRIPTION OF THE INVENTION

Figure 1:
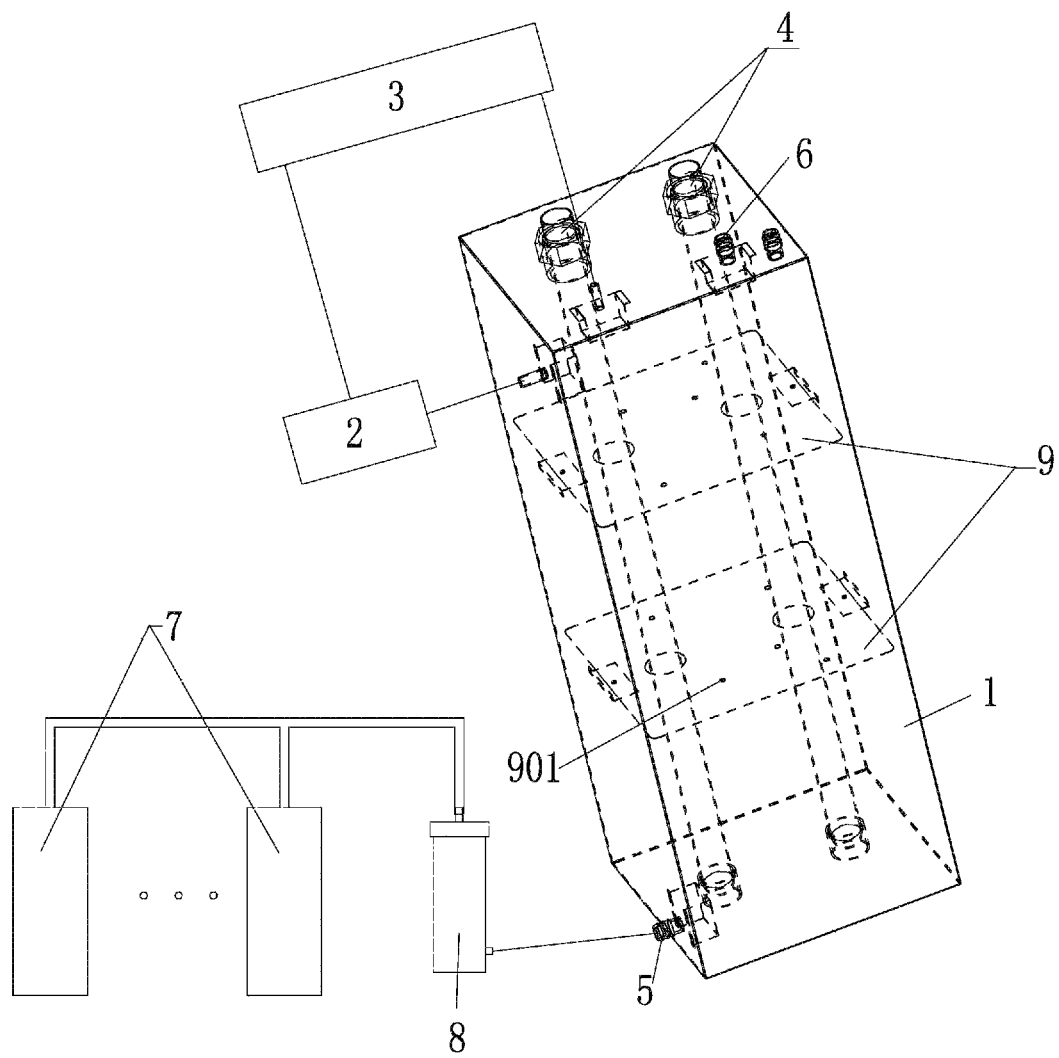
FIG. 1 is a schematic structural diagram of an embodiment of an air purifier.

Referring to FIG. 1, an air purifier includes a housing 1, a vacuum air pump 2 and an ozone generator 3, at least one ultraviolet lamp tube 4 is provided in the housing 1, an air inlet 5 is provided at a position of the housing 1 corresponding to one end of the ultraviolet lamp tube 4, at least one air outlet 6 is provided at a position of the housing 1 corresponding to the other end of the ultraviolet lamp tube 4, and an air filter unit 7 is communicated with the air inlet 5 by means of an air drying unit 8; and an air inlet end of the vacuum air pump 2 is communicated with an inner cavity of the housing 1, an air outlet end of the vacuum air pump 2 is communicated with an air inlet end of the ozone generator 3, and an air outlet end of the ozone generator 3 is communicated with the inner cavity of the housing 1. The number of the air outlet 6 is at least one, and can be configured as required.

At least one first division plate 9 is provided in the inner cavity of the housing 1 and is along the length direction of the ultraviolet lamp tube 4, and the first division plate 9 is perpendicular to the length direction of the ultraviolet lamp tube 4. The first division plate 9 is provided with one or more first through holes 901. The first division plate 9 is made of an ultraviolet resistant material, and the number of the first division plate 9 is determined according to the volume of the housing 1.

The housing 1 is cylindrical or cubic. The length direction of the housing 1 is parallel to or perpendicular to the horizontal plane.

Figure 2:
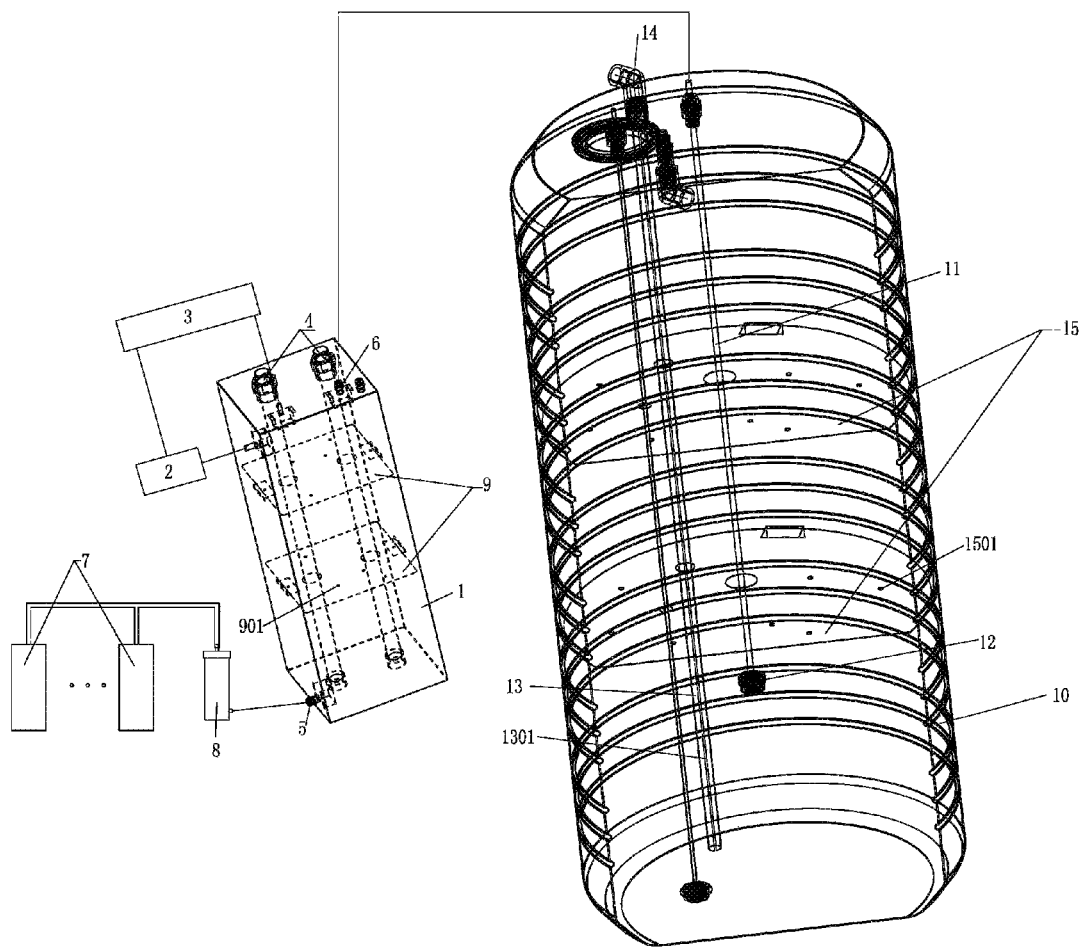
FIG. 2 is a schematic structural diagram of an embodiment of a water purification system.

As shown in FIG. 2, a water purification system includes a water purification tower 10 and further includes the air purifier, and one air outlet 6 of the air purifier is communicated with an inner cavity of the water purification tower 10.

An air duct 11 is provided in the inner cavity of the water purification tower 10, the air outlet 6 is communicated with one end of the air duct 11, and the other end of the air duct 11 is provided with a sand air-diffuser 12.

A diversion pipe 13 is provided in the inner cavity of the water purification tower 10, a top of the water purification tower 10 is provided with a purified water inlet 14, the purified water inlet 14 is communicated with one end of the diversion pipe 13, the other end of the diversion pipe 13 extends to a bottom of the water purification tower 10, and a side wall of the diversion pipe 13 is provided with a through slot 1301 along the length direction.

At least one second division plate 15 is provided in the inner cavity of the water purification tower 10 and is along the length direction of the water purification tower 10, and the second division plate 15 is perpendicular to the length direction of the water purification tower 10. The second division plate 15 is provided with one or more second through holes 1501. Mounting position of the second division plate 15 is determined as follows: a height from the full water level of the water purification tower 10 in the water purification tower 10, corresponding to the volume of purified water (ozone water) produced by a mainframe with the time of 10 to 15 minutes and delivered to the water purification tower 10, is calculated, and one second division plate 15 is mounted at this height, the second division plate 15 is in the same cross-sectional shape as the water purification tower 10, but its cross section area is slightly smaller than that of the water purification tower 10. The porous second division plate 15 is mounted in the water purification tower 10 as required by this method according to the actual water storage volume of a purified water tank.

The air purifier can be independent of the water purification tower 10, and the air purifier is placed on one side of the water purification tower 10 alone. The air purifier can also be integrated with the water purification tower 10 and is placed on the water purification tower 10. In addition, the air purifier can also provide a water production device with sterilized air carrying ozone, and is placed in a mainframe box of the water production device.

The embodiments of the present invention are described above with reference to the drawings, but the present invention is not limited to the specific embodiments. The specific embodiments described above are merely illustrative but not restrictive. Many forms may also be made by those of ordinary skilled in the art under the enlightenment of the present invention without departing from the purpose of the present invention and the scope of the claims, and these forms fall into the scope of the present invention.

The invention claimed is:

1. An air purifier, wherein comprising a housing (1), a vacuum air pump (2) and an ozone generator (3), at least one ultraviolet lamp tube (4) is provided in the housing (1), an air inlet (5) is provided at a position of the housing (1) corresponding to one end of the ultraviolet lamp tube (4), at least one air outlet (6) is provided at a position of the housing (1) corresponding to the other end of the ultraviolet lamp tube (4), and an air filter unit (7) is communicated with the air inlet (5) by means of an air drying unit (8); and an air inlet end of the vacuum air pump (2) is communicated with an inner cavity of the housing (1), an air outlet end of the vacuum air pump (2) is communicated with an air inlet end of the ozone generator (3), and an air outlet end of the ozone generator (3) is communicated with the inner cavity of the housing (1).

2. The air purifier according to claim 1, wherein at least one first division plate (9) is provided in the inner cavity of the housing (1) and is along the length direction of the ultraviolet lamp tube (4), and the at least one first division plate (9) is perpendicular to the length direction of the ultraviolet lamp tube (4).

3. The air purifier according to claim 2, wherein the at least one first division plate (9) is provided with one or more first through holes (901).

4. The air purifier according to claim 1, wherein the housing (1) is cylindrical or cubic.

5. The air purifier according to claim 1, wherein the length direction of the housing (1) is parallel to or perpendicular to the horizontal plane.

6. A water purification system, comprising a water purification tower (10), wherein further comprising the air purifier according to claim 1, one air outlet (6) of the air purifier is communicated with an inner cavity of the water purification tower (10).

7. The water purification system according to claim 6, wherein an air duct (11) is provided in the inner cavity of the water purification tower (10), the air outlet (6) is communicated with one end of the air duct (11), and the other end of the air duct (11) is provided with a sand air-diffuser (12).

8. The water purification system according to claim 6, wherein a diversion pipe (13) is provided in the inner cavity of the water purification tower (10), a top of the water purification tower (10) is provided with a purified water inlet (14), the purified water inlet (14) is communicated with one end of the diversion pipe (13), the other end of the diversion pipe (13) extends to a bottom of the water purification tower (10), and a sidewall of the diversion pipe (13) is provided with a through slot (1301) along the length direction.

9. The water purification system according to claim 6, wherein at least one second division plate (15) is provided in the inner cavity of the water purification tower (10) and is along the length direction of the water purification tower (10), and the at least one second division plate (15) is perpendicular to the length direction of the water purification tower (10).

10. The water purification system according to claim 6, wherein the at least one second division plate (15) is provided with one or more second through holes (1501).

\* \* \* \* \*